US010806698B2

(12) United States Patent
Harel et al.

(10) Patent No.: US 10,806,698 B2
(45) Date of Patent: *Oct. 20, 2020

(54) COMPOSITION FOR ORAL DELIVERY OF BIOACTIVE AGENTS

(71) Applicant: Intervet Inc., Madison, NJ (US)

(72) Inventors: Moti Harel, Pikesville, MD (US); Swetha Kambalapally, Ellicott City, MD (US)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,359

(22) Filed: Mar. 6, 2019

(65) Prior Publication Data

US 2019/0201331 A1 Jul. 4, 2019

Related U.S. Application Data

(63) Continuation of application No. 15/100,764, filed as application No. PCT/US2014/066510 on Nov. 20, 2014, now Pat. No. 10,272,036.

(60) Provisional application No. 61/912,958, filed on Dec. 6, 2013.

(51) Int. Cl.
| A61K 9/10 | (2006.01) |
| A61K 9/00 | (2006.01) |
| A61K 47/36 | (2006.01) |
| A61K 47/44 | (2017.01) |
| A61K 9/16 | (2006.01) |
| A61K 9/19 | (2006.01) |
| A61K 9/50 | (2006.01) |
| A01N 25/28 | (2006.01) |
| A01N 43/16 | (2006.01) |
| A61K 31/573 | (2006.01) |
| A61K 39/112 | (2006.01) |
| A61K 39/02 | (2006.01) |
| A61K 39/35 | (2006.01) |
| A61K 39/00 | (2006.01) |

(52) U.S. Cl.
CPC ............ A61K 9/0053 (2013.01); A01N 25/28 (2013.01); A01N 43/16 (2013.01); A61K 9/1652 (2013.01); A61K 9/19 (2013.01); A61K 9/5026 (2013.01); A61K 9/5036 (2013.01); A61K 31/573 (2013.01); A61K 39/0275 (2013.01); A61K 39/107 (2013.01); A61K 39/35 (2013.01); A61K 47/36 (2013.01); A61K 47/44 (2013.01); A61K 2039/542 (2013.01); A61K 2039/552 (2013.01); A61K 2039/57 (2013.01); A61K 2039/575 (2013.01)

(58) Field of Classification Search
CPC ............. A61K 39/107; A61K 2039/57; A61K 2039/542; A61K 9/1652; A61K 9/5036; A61K 9/5026; A61K 47/36; A61K 47/44

See application file for complete search history.

(56) References Cited

U.S. PATENT DOCUMENTS

| 5,674,495 A | 10/1997 | Bowersock et al. |
| 6,656,470 B2 | 12/2003 | Bowersock |
| 2001/0043949 A1 | 11/2001 | Delgado |
| 2003/0017195 A1 | 1/2003 | Mitragotri |
| 2008/0044481 A1 | 2/2008 | Harel |
| 2008/0113031 A1 | 5/2008 | Moodley et al. |
| 2008/0268063 A1 | 10/2008 | Jon |
| 2009/0017067 A1* | 1/2009 | Diehl ............... A61K 39/00 424/209.1 |
| 2012/0141585 A1* | 6/2012 | Coulter ............ A61K 9/1617 424/464 |
| 2012/0288552 A1* | 11/2012 | Harel .............. A61K 9/1652 424/442 |
| 2013/0259933 A1 | 10/2013 | Kamaguchi et al. |
| 2014/0017313 A1 | 1/2014 | Coulter et al. |
| 2015/0132396 A1 | 5/2015 | Coulter et al. |

FOREIGN PATENT DOCUMENTS

| EP | 2105129 A2 | 9/2009 |
| JP | H10-130166 A | 5/1998 |
| WO | 9502416 A1 | 1/1995 |
| WO | 199852547 A1 | 11/1998 |
| WO | 200012065 A1 | 3/2000 |
| WO | 2005115341 A2 | 12/2005 |
| WO | 2006035416 A2 | 4/2006 |
| WO | 2006116392 A2 | 11/2006 |
| WO | 2010111565 A2 | 9/2010 |
| WO | 20110018504 A2 | 2/2011 |
| WO | WO2011152783 A1 | 12/2011 |
| WO | WO2013126543 A1 | 8/2013 |

OTHER PUBLICATIONS

Particle Sciences; title: Encapsulation, Technical Brief, vol. 7, 2010. (Year: 2010).*
P. Sriamornsak; title: Chemistry of Pectin and Its Pharmaceutical Uses : A Review; Journal: Silpakorn University International Journal; published 2003, downloaded from www.journal.su.ac.th/index.php/suij/article/view/48/48.*
Kimica; title: Sodium Alginate, product information downloaded from https://kimica-algin.com/products/NaAlgin/ on Feb. 20, 2020.*
Cui-Yun Yua et al, Composite microparticle drug delivery systems based on chitosan, alginate and pectin with improved pH-sensitive drug release property, Colloids and Surfaces B: Biomterraces, 2009, pp. 245-249, vol. 68, Elsevier.
Kotzé, A.F. et al., Effect of the degree of quaternization of N-trimethyl chitosan chloride on the permeability of intestinal epithelial cells (Caco-2), European Journal of Pharmaceutics and Biopharmaceutics, 1999, pp. 269-274, 47.

(Continued)

Primary Examiner — Yanzhi Zhang

(57) ABSTRACT

A composition for oral administration of a bioactive agent to aquatic or terrestrial species includes particles each of which includes a bioactive agent dispersed in oil droplets, the oil droplets being dispersed in a matrix including an enteric coating polymer, wherein the particles each further include a mucoadhesive polymer. Methods of making and using the composition are also provided.

20 Claims, No Drawings

(56) References Cited

OTHER PUBLICATIONS

Kulkarni, A.D. et al., N,N,N-Trimethyl chitosan: An advanced polymer with myriad of opportunities in nanomedicine, Carbohydrate Polymers, 2017, pp. 875-902, 157.
Lian-Yan Wang et al, Preparation and characterization of uniform-sized chitosan microspheres containing insulin by membrane emulsification and a two-step solidification process, Colloids and Surfaces B:, 2006, pp. 126-135, vol. 50, Elsevier.
Extended European Search report for application No. 14868228.9, dated Aug. 22, 2017, 7 pages.
Li, X.Y., et al., "Preparation of alginate coated chitosan microparticles for vaccine delivery," Nov. 19, 2008, pp. 1-11, vol. 8(89), BMC Biotechnology.
Danish Search Report for Danish Application No. PA 2016 70506, dated May 3, 2017, 6 pages.
Danish Office Action for Danish Application No. BA 2016 00092, dated Feb. 6, 2017, 2 pages.
U.S. Response to Office Action for U.S. Appl. No. 13/390,085, dated Apr. 6, 2016, 24 pages.
European Response to Office Action for EP Application No. 10749625.9, dated Nov. 18, 2016, 10 pages.
Vietnam Office Action for Vietnam Application No. 1-2016-02489, dated Nov. 23, 2016, 2 pages.
Russian Office Action dated Sep. 15, 2016 for Russian Application No. a 20160251, including English translation, 6 pages.
International Search Report and Written Opinion of the International Searching Authority for International Application No. PCT/US2014/066510, 12 pages.
International Preliminary Report on Patentability for International Application No. PCT/EP2014/066510, dated Jun. 7, 2016, 9 pages.
Masuda, K et al., Oral-antigen delivery via a water-in-oil emulsion system modulates the balance of the Th1/Th2 type response in oral tolerance, Pharmaceutical Research, 2003, pp. 130-134, 20(1).
Particle Sciences, Title: Encapsulation, Technical Brief, vol. 7, 2010.
Sriamornsak, P, Chemistry of Pectin and its Pharmaceutical Uses: A Review Journal, Silpakorn University International Journal, 2003, pp. 206-228.
Tal Shechter, "3 Differences between oil-in-water & water-in-oil emulsions", BEE International Blog posted Jul. 12, 2016, downloaded from http://www.beei.com/blog/3-differences-betwee-oil-in-water-water-in-oil-emulsions.

* cited by examiner

COMPOSITION FOR ORAL DELIVERY OF BIOACTIVE AGENTS

CROSS-REFERENCE TO RELATED APPLICATIONS

This application is a Continuation application of U.S. application Ser. No. 15/100,764, filed on Jun. 1, 2016, now U.S. Pat. No. 10,272,036 B2, which was filed as a national stage entry under 35 U.S.C. § 371 of PCT/US2014/066510, which was filed on Nov. 20, 2014, which claims priority benefit of U.S. Application No. 61/912,958, filed on Dec. 6, 2013, the entirety of which is incorporated herein by reference.

BACKGROUND OF THE INVENTION

Oral administration of drugs and vaccines offers several advantages. Dosages could be administered to a large number of animals via the food or water with minimal restraint and labor. Restraint also stresses animals rendering the drug or vaccination less effective and increasing the risk of infectious disease. For meat-producing animals, oral administration has another advantage in that it avoids injection site reactions. Broken needles, contamination of the injection site, or the use of highly reactive adjuvants can induce abscesses that damage the carcass and the skins. These reactions decrease the value of the animal at slaughter. This is also an issue in fish vaccination programs where fish need to be harvested from their tanks or open sea cages and injected individually. Oral inoculation is quick and efficient and eliminates the need for multiple handling of animals to administer subsequent booster inoculations. Adverse immune reactions following oral administration are also much less likely to occur and are therefore safer.

Oral vaccination is a particularly cost effective way to vaccinate or treat a large number of fish at one time in fish aquaculture systems, with minimal stress or labor. This is especially true when oral administration of the vaccine can be effected through ingestion during the course of feeding/drinking. Further, oral vaccines can be manufactured more cost effectively than injectable vaccine formulations because of the fewer purification steps needed to generate an oral vaccine. Oral vaccination also offers the advantage of fewer side effects such as stress or other reactions to the injection.

Despite the advantages of oral administration of drugs and particularly vaccines, the development of the technology has been delayed by the lack of adequate vaccine delivery systems. In the absence of suitable delivery systems, most oral vaccines undergo degradation in the gastrointestinal (GI) tract, especially under low-pH stomach conditions, resulting in limited absorption, which in turn results in insufficient immune responses.

Historically, immunization has relied on the induction of humoral immunity by parenteral administration of vaccines. Antibodies induced by parenteral administrations do not, however, necessarily reach mucosal surfaces, the sites of entry of most infectious agents. Mucosal immunity, which develops at mucosal surfaces including the intestine, lung, mouth, eye, mammary gland, and the genitourinary tract, and also skin and gill in fish, as a result of contact of antigen with mucosal tissues, is an important first line of defense against infectious agents.

Various vehicles have been developed to deliver drugs or vaccines to the gut-mucosal tissues. Biodegradable polymers, such as poly-(DL-lactide) and poly-(DL-lactide-co-glycolide), have been used to produce compositions for oral administration of antigens. However, production of these polymer particles requires the use of solvents that can harm fragile antigens. Furthermore, the use of solvents prevents the incorporation of attenuated live organisms, such as viruses or bacteria, within those compositions.

Other challenges of developing adequate oral delivery systems include the need to select only food or feed grade and biodegradable compounds and adjuvants, and the need for a long-lasting and robust immune response.

SUMMARY OF THE INVENTION

In one aspect, the invention provides a composition for oral administration of a bioactive agent to aquatic or terrestrial species, including particles each of which includes a bioactive agent dispersed in oil droplets, the oil droplets being dispersed in a matrix including an enteric coating polymer, wherein the particles each further include a mucoadhesive polymer.

In another aspect, the invention provides a method of post gastric delivery of a bioactive agent to an animal, including a step of orally administering to the animal a composition as described above, wherein the bioactive agent is an immunogen.

In another aspect, the invention provides a method of vaccinating aquatic or terrestrial species, including a step of orally administering to the species a composition as described above, wherein the composition is a delivery vehicle for a vaccine.

In another aspect, the invention provides a method of preparing a composition. The method includes, in sequence:

(a) forming an aqueous mixture including a dispersed or dissolved bioactive agent;

(b) homogenizing the aqueous mixture of step (a) in oil to produce an emulsion of the aqueous mixture in the oil;

(c) forming a slurry of the product of step (b) in an aqueous solution including an enteric coating polymer; and either (d1) spraying, dropping or injecting the slurry of step (c) into an aqueous solution containing a crosslinking agent for the enteric coating polymer to form the particles, wherein the aqueous mixture of step (a) further includes a mucoadhesive polymer, or (d2) forming the particles from the slurry of step (c), wherein step (b) further includes forming droplets of the emulsion in aqueous mucoadhesive polymer and crosslinking the mucoadhesive polymer to form intermediate particles.

DETAILED DESCRIPTION OF THE INVENTION

Unless otherwise defined herein, scientific and technical terminologies employed in the present disclosure shall have the meanings that are commonly understood and used by one of ordinary skill in the art. Also, as used herein and in the claims, the terms "at least one" and "one or more" have the same meaning and include one, two, three or more. Unless otherwise indicated, percentages or parts of components in compositions are on a weight basis. The term "dispersed" means suspended and/or dissolved.

"Oral vaccination" is defined as the oral administration through the diet of immunogenic material to stimulate the systemic immune system of an animal to develop a specific immune response to a pathogen.

"Crosslink" and variants thereof refers to the linking of two or more materials and/or substances, including any of those disclosed herein, through one or more covalent and/or non-covalent (e.g., ionic) associations. Crosslinking may be effected naturally (e.g., disulfide bonds of cystine residues) or through synthetic or semi-synthetic routes. Crosslinking of charged polymers can be effected by ionic association with a polyvalent counterion of opposite charge. Firm, solid structures, for example hydrogels, can be prepared by such crosslinking.

"Gastric protection" refers to the protection of a bioactive agent from gastric destruction and loss of activity.

The compositions of the invention include particulate materials comprising a bioactive agent and a mucoadhesive polymer, wherein the bioactive agent is dispersed in an oil. The oil droplets are in turn embedded in, or coated by, an external matrix of an enteric coating polymer. The external matrix surrounds the oil droplets, protecting the contents from exposure to low pH conditions in the animal's stomach, since the polymer remains insoluble at low pH and remains intact as a protective coating or layer. The particles typically have an average geometric size (sometimes referred to as diameter) in a range of 10 to 5000 μm, and may either be formed directly in that size range or reduced to that size by milling, grinding, or other means. Usually, the particles have a diameter of less than 100 μm, preferably less than 50 μm.

In some embodiments, the mucoadhesive polymer and the bioactive agent are mixed together and in mutual contact, associated together within particles that are in turn dispersed in the oil droplet. One or more of these particles are present within a single oil droplet, and one or more oil droplets are present within the external matrix. The mucoadhesive polymer and/or the enteric coating polymer may be crosslinked or not.

In other embodiments, the bioactive agent is dispersed as above within oil droplets, and these are then embedded in the mucoadhesive polymer. The resulting particles are in turn embedded in the external matrix of enteric coating polymer. The mucoadhesive polymer and/or the enteric coating polymer may be crosslinked or not.

In some embodiments the invention provides a composition for oral administration of a vaccine to stimulate an immune response in aquatic and terrestrial species against specific diseases. The composition comprises an effective amount of an antigen as the bioactive agent. The present compositions are designed to present the bioactive material for contact with the gut mucosa of the animal to stimulate uptake and mucosal immunity. Compositions according to this invention are administered orally, typically with a feed or pharmaceutically acceptable carrier, including, for example, water (e.g., animal drinking water), tablets, capsules, bolus dosage forms, feed pellets or as a food additive to carry the composition into the gut of the targeted species.

The compositions of the invention provide several advantages in delivering a bioactive agent to a subject. First, the method of making the delivery system eliminates the use of organic solvents or high temperature and pH which are often required for the preparation of particles by other methods. By maintaining an aqueous environment at mild pH conditions and low temperatures throughout the preparation of the present composition, sensitive bioactives such as live attenuated bacteria or viruses can be orally delivered. Second, the additional layer of enteric coating polymer protects the bioactive agent against degradation in the gastrointestinal tract. In the case of an immunogen, this allows stimulation of the same immune response with a smaller amount of antigen/vaccine. Third, the oil dispersion encloses the bioactive agent, preventing small bioactive molecules such as proteins, peptides and drugs from leaching to an aqueous environment during preparation, as well as during gastric exposure. Further, mucoadhesive polymer itself provides an adjuvant effect. Finally, the delivery system can be easily formulated for efficient delivery to both aquatic and terrestrial species.

Typically, all components used in preparing the inventive compositions are food grade, non-toxic and biodegradable, and typically naturally occurring. A description of materials useful for preparing the compositions follows.

Bioactive Agent

The bioactive agent may be a naturally occurring, synthetic, or semi-synthetic material (e.g., compounds, fermentates, extracts, cellular structures) capable of eliciting, directly or indirectly, one or more physical, chemical, and/or biological effects. The bioactive agent may be capable of preventing, alleviating, treating, and/or curing abnormal and/or pathological conditions of a living body, such as by destroying a parasitic organism, or by limiting the effect of a disease or abnormality. Depending on the effect and/or its application, the bioactive agent may be a pharmaceutical agent (such as a prophylactic agent or therapeutic agent), a diagnostic agent, and/or a cosmetic agent, and includes, without limitation, vaccines, drugs, prodrugs, affinity molecules, synthetic organic molecules, hormones, antibodies, polymers, enzymes, low molecular weight molecules proteinaceous compounds, peptides, vitamins, steroids, steroid analogs, lipids, nucleic acids, carbohydrates, precursors thereof, and derivatives thereof. The bioactive agent may also be a nutritional supplement. Non-limiting nutritional supplements include proteins, carbohydrates, water-soluble vitamins (e.g., vitamin C, B-complex vitamins, and the like), fat-soluble vitamins (e.g., vitamins A, D, E, K, and the like), minerals, and herbal extracts. The bioactive agent may be commercially available and/or prepared by known techniques.

Bioactive agents in the present invention include, without limitation, vaccines (vaccines can also be delivered as part of immune-stimulating complexes, conjugates of antigens with cholera toxin and its B subunit, lectins and adjuvants), antibiotics, affinity molecules, synthetic organic molecules, polymers, low molecular weight proteinaceous compounds, peptides, vitamins, steroids, steroid analogs, lipids, nucleic acids, carbohydrates, precursors thereof, and derivatives thereof. The bioactive agent may also be a pesticide, for example a rodenticide.

The bioactive agent may be an immunogen, i.e., a material capable of mounting a specific immune response in an animal. Examples of immunogens include antigens and vaccines. For example, immunogens may include immunogenic peptides, proteins or recombinant proteins, including mixtures comprising immunogenic peptides and/or proteins and bacteria (e.g., bacterins); intact inactive, attenuated, and infectious viral particles; intact killed, attenuated, and infectious prokaryotes; intact killed, attenuated, and infectious protozoans including any life cycle stage thereof, and intact killed, attenuated, and infectious multicellular pathogens, recombinant subunit vaccines, and recombinant vectors to deliver and express genes encoding immunogenic proteins (e.g., DNA vaccines).

The one or more bioactive agents typically constitute at least 0.1% of the weight of the particles, excluding water, or at least 1%, or at least 5%. Typically, they constitute at most 40%, or at most 20%, or at most 10%.

Mucoadhesive Polymer

The mucoadhesive polymer is a polymer that specifically binds to mucosal tissues, and helps retain the bioactive agent in close proximity to the mucosa, thereby improving administration. Suitable examples include synthetic polymers such as poly(acrylic acid), hydroxypropyl methylcellulose and poly(methyl acrylate), carboxylic-functionalized polymers, sulfate-functionalized polymers, amine-functionalized polymers, and derivatives or modifications thereof, as well as naturally occurring polymers such as carrageenan, hyaluronic acid, chitosan, cationic guar and alginate. Derivatized or otherwise modified versions of naturally occurring polymers may also be used, and many such polymers are known in the art. Nonlimiting examples include propylene glycol alginate and pectins, carboxymethyl chitosan, carboxymethylchitin, methyl glycol chitosan, trimethyl chitosan and the like.

A preferred mucoadhesive polymer is chitosan and modified or derivatized chitosan, which can be obtained through the deacetylation of chitin, the major compound of exoskeletons in crustaceans. Chitosan [a-(1~4)-2-amino-2-deoxy-β-D-glucan], a mucopolysaccharide closely related to cellulose, exhibits chemical properties that are determined by the molecular weight, degree of deacetylation, and viscosity. Chitosan can form microparticles and nanoparticles that can bind large amounts of antigens by chemical reaction with crosslinking agents such as phosphate ions, glutaraldehyde or sulfate ions.

Although chitosan is used in some preferred embodiments, other polymers may be used to achieve a similar mucoadhesive function. These include but are not limited to gelatin, alginate, dextran, hyaluronic acid, agar, and resistant starch.

The one or more mucoadhesive polymers typically constitute at least 1% of the weight of the particles, excluding water, or at least 10%, or at least 15%. Typically, they constitute at most 50%, or at most 30%, or at most 20%.

Oil

In typical traditional products, a significant amount of bioactive agent is lost to the aqueous environment by leaching out of the particle during its preparation and through the gastric passage, particularly small molecular size bioactive agents such as viruses, proteins, drugs, antibiotics, pesticides and the like. In the present invention, leaching of bioactive agent from the particle is largely eliminated by discrete particles, domains or phases containing the agent being dispersed in, or coated by, an oil. Any type of oil, including vegetable, animal or synthetic oils and fats in either liquid or solid form, or waxes, can be used for coating the bioactive agent. Vegetable origin oils used in the present invention include, without limitation, castor oil, coconut oil, coco butter, corn oil, cottonseed oil, olive oil, olive squalane, palm oil, peanut oil, rapeseed oil, safflower oil, sesame oil, soybean oil, sunflower oil, stearate, carnauba wax and mixtures thereof. Animal origin oils used in the present invention include, without limitation, fish oil, shark squalane, butterfat, beeswax, lanolin, lard and the like. In some cases the dispersing oil is a mixture of olive or shark squalanes with any other type of oil, fat or wax. Typically, the mass of oil is greater than the combined mass of bioactive agent and mucoadhesive polymer.

In a typical procedure, an aqueous solution containing the bioactive agent and mucoadhesive polymer is homogenized with oil at a ratio of one part solution to 1.1-5 parts oil by weight until a uniform emulsion is produced. To assist in the formation of a uniform and stable emulsion, a nonionic surfactant may be added. Suitable nonionic surfactants, without limitation, include ethoxylated aliphatic alcohol, polyoxyethylene surfactants and carboxylic esters, etc. Once a stable emulsion is formed, the aqueous droplets dispersed in the oil are solidified by a chemical or physical reaction of the mucoadhesive polymer. For example, gelatin and agar polymers are solidify by dropping the temperature or changing the pH of the emulsion; while chitosan is solidified by raising the pH of the emulsion to above 6.5 and/or by adding counterions such as sodium tripolyphosphate (TPP).

The one or more oils typically constitute at least 1.5% of the weight of the particles, excluding water, or at least 10%, or at least 20%. Typically, they constitute at most 40%, or at most 30%, or at most 25%.

Enteric Coating Polymer

Droplets of the oil dispersion, either containing or coated by the mucoadhesive polymer, are dispersed in a matrix of enteric coating polymer that provides gastric protection and intact post gastric release or delivery of the bioactive agent, i.e., release in the intestine.

Exemplary enteric coating polymers include polymers soluble in water at sufficiently high pH, but insoluble at low pH. Typically, they are soluble at a pH greater than 5.0, and insoluble at a pH less than 4.0. Suitable polymers are substantially soluble or digestible under the relatively mild pH conditions of an animal's intestine, where the bioactive material is to be released, but insoluble and indigestible in the stomach, where the external matrix of enteric coating polymer protects the sensitive bioactive agent from deterioration. In some cases, the enteric coating polymer is crosslinked, for example with divalent cations, to prevent dissolution or digestion in the stomach.

Suitable enteric coating polymers can be selected from any of a wide variety of hydrophilic polymers including, for example, polyacrylic acid, poly(meth)acrylates, carboxymethyl cellulose, methyl cellulose, cellulose acetate phthalate and water soluble, natural or synthetic polysaccharide gums. One exemplary synthetic enteric coating polymer is EUDRAGIT® FS30D (Evonik Industries). Sodium alginate and pectins are preferred water soluble gums, because of their mild crosslinking conditions.

Alginates provide a preferred hydrophilic carrier matrix for gastric sensitive bioactive agents, particularly due to their ease of use in forming solid gel compositions. Alginate solutions form solid gels when combined or mixed with divalent cations. Nonetheless, in some embodiments the alginate is not crosslinked, but remains indigestible and insoluble in a gastric environment and therefore protective of the particle contents while under the low pH conditions of an animal's stomach.

Alginates comprise varying proportions of 1,4-linked β-D-mannuronic acid (M), α-L-guluronic acid (G), and alternating (MG) blocks. The viscosity of alginate solutions is mostly determined by the molecular ratio of M/G blocks. Low viscosity alginates typically contain a minimum of 50% mannuronate units and their viscosity ranges from 20-200 mPa. Medium and high viscosity alginates contain a minimum of 50% of guluronic acid units and their viscosity is typically over >200 mPas.

In some embodiments the matrix forming polymer is alginate, pectin or a mixture thereof. Low viscosity grade alginates and low methoxy pectins are preferred. Typical low methoxy pectins have a methylation degree below 50%, and these are typically crosslinked with a divalent cation such as Ba, Ca, Mg, Sr or Zn.

The one or more enteric coating polymers typically constitute at least 10% of the weight of the particles, excluding water, or at least 20%, or at least 30%. Typically, they constitute at most 70%, or at most 50%, or at most 40%.

Optional Ingredients In some embodiments the composition optionally includes nutrients, nutraceuticals, feed attractants and/or taste masking compounds, in addition to the primary bioactive agent. Penetration enhancers or adjuvants may also be included, to elicit a strong immune response and improve the antigen taken up by mucosal lymphocytes. One exemplary adjuvant is beta glucan.

Making the Compositions

A first general way of making the particles is as follows. An aqueous mixture comprising a dispersed bioactive agent and mucoadhesive polymer is homogenized with oil to produce an emulsion of the aqueous mixture in the oil. Typically, a ratio of 1 part aqueous mixture to 1.1-5 parts oil by weight is used in making the emulsion. The emulsion is then slurried in an aqueous solution comprising an enteric coating polymer, and the slurry is sprayed, dropped or injected into an aqueous solution containing a crosslinker for the enteric coating polymer, thereby forming the particles.

In a second general method, an aqueous mixture comprising a dispersed bioactive agent is homogenized with oil to produce an emulsion of the aqueous mixture in the oil. Typically, a ratio of 1 part aqueous mixture to 1.1-5 parts oil by weight is used in making the emulsion. Droplets of the emulsion are then dispersed in aqueous mucoadhesive polymer, which is crosslinked to form intermediate particles that may optionally be separated from the crosslinking solution. The isolated or non-isolated intermediate particles are then slurried in an aqueous solution comprising an enteric coating polymer. The particles are formed by spray drying, or by freeze drying and milling.

In one specific method of making the compositions, an oil containing dispersed particles of bioactive agent associated with the mucoadhesive polymer is slurried into a 5-15% solution of low viscosity grade sodium alginate, optionally including 1-3% of low methoxy pectins, and the slurry is injected, dropped or spray atomized into an aqueous solution of divalent cations such as calcium chloride. The size of the resulting matrix particles can be adjusted by the rate and method of delivery of the alginate dispersion into the calcium chloride solution. In another embodiment the slurry is dried without crosslinking the alginate, using any drying method known in the art, for example spray drying or vacuum drying. Typically the resultant particles range in size from about 20 μm to about 8 millimeters, more typically from about 50 μm to about 1000 μm.

In an alternative specific method, 0.5-2% of an insoluble source of divalent cations such as $CaCO_3$ is added to the slurry of bioactive agent-containing oil droplets in sodium alginate solution, followed by adding 0.5-1% of a weak organic acid such as glucono-delta-lactone (GDL) as an acidifier to slowly release the cations, such as calcium ions. The cations crosslink the alginate to form a solid cake gel, which can be chopped or crushed into small chunks or particles. Typically the resultant chunks or particles range in size from about 50 μm to about 10 millimeters, more typically from about 100 to about 5000 μm. The skilled practitioner will recognize that other natural or synthetic polymers, preferably anionic polymers, can be utilized using ionic interaction-based affinity, forming the basis of the present compositions.

Using the Compositions

The compositions of this invention can be stored in aqueous suspension or dried by any drying method known in the art, and stored in a dehydrated state for long periods of time without a significant loss of activity.

Compositions according to the invention can be administered orally as a component of drinking water, as a food additive, or as part of a vaccine formulation containing a pharmaceutically acceptable carrier and optional adjuvants. Alternatively, the present compositions can be included in other standard oral dosage forms. Those skilled in the art will appreciate that there is a wide variety of art-recognized food, feed, nutraceutical or pharmaceutical dosage forms and acceptable carriers, suitable for delivering the composition to the targeted animal.

Administration of the compositions in accordance with this invention can be effected in single or multiple dose protocols. In one embodiment, immunogenic compositions are administered in multiple dose protocols administered over a period of about 3 days to about 10 days or longer, and can be repeated periodically as the target species evidences loss of immunity.

For applications in drinking water for use in swine, poultry, cattle or aquatic animals, additional oil or inert polypropylene or polyester particles can be incorporated in the composition to increase buoyancy (I.e., decrease density) so that watering devices for delivery in fish culture tanks could be used to deliver the present compositions. Thus, the compositions can be administered to animals either as a component of their daily feed or as a component of their drinking water.

EXAMPLES

Example 1a

Preparation of the Composition of the Invention

An inventive composition was prepared as follows. Three grams of mucoadhesive polymer (Chitosan, FMC Biopolymers Inc.) was dissolved in 100 ml of 0.5N glacial acetic acid solution at 50° C. The pH of the solution was adjusted to 5.8 with sodium hydroxide and the solution allowed to cool down to room temperature. Tween 80 (0.2%, Sigma, St Louis, Mo.) and Antifoam (0.5%, Sigma, St Louis, Mo.) were added and the chitosan solution kept at 4° C. until use. A 30 ml solution containing 300 mg ovalbumin ("OVA", a model vaccine) was added to the chitosan solution to produce a mixture. The resulting solution was added to 195 g olive oil containing 5% Span-80 (Sigma) and homogenized at 10,000 rpm for 30 min in an ice bath to form a water in oil emulsion. A 20 ml aqueous sodium tripolyphosphate (5%) and 0.5N NaOH was slowly added with mixing to the bioactive agent emulsion containing ovalbumin and crosslinked chitosan microparticles in a continuous oil phase. The particles were allowed to harden for at least 2 h but not removed from the oil phase.

The dispersion of particles in oil was stirred into 330 ml of a 9% aqueous solution of low viscosity grade sodium alginate (FMC Biopolymers Inc.) that also contained 66 g oligosaccharides (instant inulin, Cargill, Minneapolis, Minn.), 10 g lecithin and 3 g Tween-80. The resulting aqueous dispersion was injected into a cross-linking solution containing 5% $CaCl_2$ to form alginate matrix beads, each containing multiple oil droplets that in turn each contained microparticles of ovalbumin and crosslinked chitosan. The beads were freeze dried and milled below 150 μm sized particles to obtain a dry composition of the present invention.

Example 1b

An alternative method of forming compositions of the invention utilizes an emulsion of an aqueous bioactive solution in an oil. Ten ml of an aqueous solution containing 100 mg ovalbumin was combined with 15 g canola oil containing 5% Span-80 and homogenized to form a fine water in oil emulsion. The emulsion was mixed with a 100 ml of 3% aqueous chitosan solution, and the dispersion was injected into a cross-linking solution containing 5% tripolyphosphate solution (5% TPP). The particles were allowed to harden for at least 2 h. The resulting solid crosslinked chitosan particles contained embedded oil droplets, and each of these oil droplets in turn contained dispersed smaller than 10 μm droplets of the aqueous ovalbumin. The solid particles were isolated by filtration and were finely dispersed in 400 ml of an aqueous solution of 9% low viscosity grade alginate. The resulting aqueous dispersion was injected into a cross-linking solution containing 5% $CaCl_2$ to form alginate matrix beads. The beads were freeze dried and milled below 150 μm sized particles to obtain a dry composition of the present invention.

Example 2

Preparation of an Immunogenic Composition

Chitosan (3 g, FMC Biopolymer) was dissolved in 100 ml solution of 0.5N glacial acetic acid at 50° C. The pH of the solution was adjusted to 5.8 with sodium hydroxide and the solution was allowed to cool to room temperature. A 10 ml solution containing 100 mg ovalbumin (OVA) as a model vaccine was mixed with 50 mg of immune-stimulating agent (beta glucan, AHD international, Atlanta, Ga.) and added into the chitosan solution. The resulting mixture was emulsified in 150 g shark squalane oil (Jedwards International) containing 5% w/w Span-80 at 10,000 rpm for 30 minutes to form an emulsion of aqueous droplets of OVA, chitosan and beta glucan in a continuous oil phase. The emulsion was added with stirring to 400 ml of an aqueous solution of 9% low viscosity grade sodium alginate in 0.5N NaOH that also contained oligosaccharides (40 g, instant inulin). The resulting emulsion was injected into a 5% $CaCl_2$ solution to crosslink the alginate, resulting in an immunogenic composition of the current invention. The composition was freeze dried and milled to particles less than 250 μm in size.

Example 3

Preparation of a Composition for Treatment/Prevention of Parasitic Infection of Fish A composition containing a protein antigen or parasiticidal compound for treatment of parasite infestation in fish is prepared. Ten mg of the bioactive agent is dissolved in 10 ml of 3% aqueous chitosan solution as described in Example 2 above, and emulsified in 15 g of oil mixture containing 75% olive oil, 20% squalane oil and 5% Span-80.

One ml of an aqueous 5% sodium tripolyphosphate, 0.5N NaOH solution is emulsified in one g olive oil and mixed into the bioactive agent emulsion, resulting in a dispersion in oil of particles containing the bioactive agent and crosslinked chitosan. The dispersion is allowed to stand for 2 h to harden the crosslinked chitosan. The resulting dispersion of particles in oil is added with stirring to a 20 ml solution containing 9% low viscosity grade sodium alginate, 1% low methoxypectin, 30% w/w instant inulin and 1% Tween-80. The resulting mixture is injected into a cross-linking solution containing 3% $CaCl_2$ to form beads of an alginate-pectin matrix containing embedded dispersed oil droplets each in turn containing microparticles of bioactive and crosslinked chitosan. The beads are freeze dried and milled to below 150 μm to obtain a dry composition of the present invention.

Example 4

Preparation of a Composition Containing a Pharmaceutical Drug

A composition containing a pharmaceutical drug (a glucocorticoid such as dexamethasone or methyl prednisolone) for treatment of colonic diseases is prepared. The drug is added to chitosan solution as described in Example 1 or 2 above, and emulsified in a mixture of 95% squalane oil and 5% Span-80. An alkali emulsion containing 5% sodium tripolyphosphate in 0.5N NaOH in squalane oil is prepared and slowly mixed (20% w/w) into the bioactive emulsion to crosslink the chitosan, and the mixture is allowed to stand for at least 2 h to harden the crosslinked particles. The oil dispersion of chitosan microparticles is mixed into a liquid containing the enteric coating polymer (30% w/w EUDRAGIT® FS30D, Evonik Industries) at a ratio of 1:3 emulsion/Eudragit liquid and spray-dried to form a dry particulate composition of the present invention.

Example 5

Encapsulation Efficiency of a Bioactive Agent in the Composition of the Current Invention The effect of the additional oil dispersion and enteric coating polymer matrix in the composition of the current invention was evaluated using ovalbumin (OVA) to simulate a typical protein drug or vaccine. Three OVA (Sigma) containing compositions were prepared. Composition 1 consisted of OVA bound chitosan microparticles, prepared by dissolving 100 mg OVA in 10 ml of 3% chitosan solution and injecting the solution into 10% aqueous TPP to form crosslinked beads, followed by a 2 h hold to harden the beads and subsequent freeze drying and milling. Composition 2 was made by emulsifying a 10 ml aqueous solution containing 100 mg OVA in 15 g of squalane oil containing 3% Span-80, and mixing the resulting emulsion in 20 ml of 3% chitosan solution. The resulting slurry was then injected into a 10% TPP solution to form beads, followed by hardening, freeze drying and milling as above. Composition 3 consisted of OVA bound chitosan microparticles according to the invention, prepared as in Example 2.

The encapsulation efficiency of OVA in the three types of composition was determined as follows. Five hundred mg of each composition was dispersed in 10 ml RIPA buffer and incubated at room temperature for 30 min. The suspensions were vortexed for 5 min and then centrifuged at 3000 rpm for 15 min. The supernatant was assayed for OVA content using Western Blot analysis, as follows.

Western Blot: the compositions were lysed with RIPA buffer as described above, and a calculated amount equivalent to 12 μg of protein per sample was loaded on a 10% SDS-polyacrylamide gradient gel (SDS-PAGE, Bio-Rad, Hercules, Calif.). Proteins were transferred onto a PVDF membrane (Blo-Rad) and blocked for 1 h with 5% non-fat milk in PBS containing 0.5% Tween-20 (PBS-T). Blots were incubated with an appropriate primary antibody at 1:5000 dilutions for 1 h at room temperature. After washing with PBS-T (3×10 mL, 5 min. each), the membranes were incubated with an appropriate HRP-conjugated secondary antibody (EMD Millipore Corporation, Billerica, Mass., USA) at 1:5000 dilution for 1 h. After washing with PBS-T (3×10 mL, 5 min. each), chemiluminescent films were developed with an ECL substrate (Amsheram Biosciences). The encapsulation efficiency of OVA (% retention of the original amount of OVA) is presented in Table 1.

TABLE 1

| Composition | Encapsulation Efficiency (%) |
|---|---|
| 1 | 70 |
| 2 | 95 |
| 3 | 95 |

The results demonstrate the protective effect of the oil dispersion in compositions 2 and 3 in preventing the leaching (loss) of the bioactive agent to a simple aqueous environment. However, significant differences between comparative Composition 2 and inventive Composition 3 were found when tested under gastric conditions, as described below in Example 7.

Example 6

Degradation of Unprotected Protein Antigen Activity in Simulated Gastric Juice

To evaluate the loss of activity of a protein antigen following a typical gastric exposure, non-encapsulated OVA (10 mg) was incubated in 10 ml simulated gastric fluid containing 0.08% pepsin at pH-2 for 2 h at 37° C. on a shaker. Medium was withdrawn at 15 min, 30 min, 60 min and 120 min incubation times, and the amount of residual OVA was analyzed using Western Blot analysis as described above. Table 2 shows the degradation of OVA over 2 h exposures in simulated gastric juice, indicated as % remaining activity relative to pre-exposure activity.

TABLE 2

| Time (min) | Remaining activity (%) |
|---|---|
| 15 | 61 |
| 30 | 55 |
| 60 | 38 |
| 120 | 2 |

These results demonstrate that the activity of unprotected protein-based antigen or bioactive agent will be completely degraded in the animal digestive tract.

Example 7

Gastric Protection of a Bioactive Agent in the Composition of the Current Invention To evaluate the remaining activity of a protein antigen after gastric exposure, three compositions were prepared as described in Example 5. Five hundred mg each of the three compositions were incubated in 10 ml simulated gastric fluid containing 0.08% pepsin at pH-2 for 2 h at 37° C. on a shaker. At the end of 2 h exposure, the gastric solutions were withdrawn and the remaining activity of the OVA in the compositions was measured as described in Example 5. Table 3 shows the remaining activity of OVA in each of the compositions after 2 h exposure to simulated gastric juice.

TABLE 3

| Composition | Remaining activity (%) |
|---|---|
| 1 | 10 |
| 2 | 20 |
| 3 | 90 |

These results clearly demonstrate the superior gastric protective effect of inventive Composition 3 relative to prior art Compositions 1 and 2.

Example 8

The Effect of the Viscosity Grade of Alginate in the Composition on Gastric Protection Three compositions containing 9% low grade viscosity alginate (50 cP), 6% medium grade viscosity alginate (300 cP) and 1% high grade viscosity alginate (800 cP) were prepared according to Example 2 above. The three compositions were exposed to simulated gastric juice as described in Example 7 and the remaining activity of the OVA in the compositions measured as described in Example 5. Table 4 shows the remaining activity of OVA in each of the compositions after 2 h exposure to simulated gastric juice.

TABLE 4

| Alginate viscosity grade | Remaining activity (%) |
|---|---|
| High (800 cp) | 25 |
| Medium (300 cp) | 40 |
| Low (50 cp) | 90 |

These results demonstrate that compositions containing lower viscosity grade alginate provide higher protection of a protein-based antigen or bioactive in the simulated animal digestive tract.

Example 9

Optimal Particle Size of the Inventive Composition

In this example the protecting effect of the particle size of a dried and milled inventive composition in a simulated gastric environment was assessed. An OVA composition was prepared as described in Example 5, followed by separating the dry powder into 2 particle sizes: small particles that went through a 50 μm screen, and large particles that were captured on the 50 μm screen but passed through a 100 μm screen. Table 5 shows the remaining activity of OVA in each particle size of the composition after 2 h exposure in simulated gastric juice.

TABLE 5

| Particle size | Remaining activity (%) |
|---|---|
| 50-100 μm | 90 |
| <50 μm | 40 |

These results show that optimal gastric protection is provided when the dry composition is milled to a particle size above 50 μm.

Example 10

Oral Administration of OVA Composition to Mice

Ovalbumin is orally administered to mice to test the efficacy of the inventive compositions in inducing an immune response.

Animals: Ten-twelve week old female BALB/C mice are used. Mice are fed ad libitum. Each experimental group is housed in a separate cage.

Ovalbumin composition: Ovalbumin (1 mg/g of ovalbumin, Sigma, St. Louis, Mo.,) is incorporated into the inventive composition as described in Example 5. Three groups of 4 mice each are inoculated as follows: 1) ovalbumln (OVA) in the composition, administered orally, 2) OVA solution, administered subcutaneously (SC),
3) antigen free composition administered orally. Mice are inoculated at 0 and 3 weeks. Each dose administers a total 100 mg of dry composition mixed with corn oil at a ratio of 1:2 w/w of dry composition/oil, coated onto feed pellets. At week 4 each mouse is euthanized and serum and spleen cells are harvested.

Immunological assays: Serum is assayed for IgG and IgA by ELISA. ELISA is performed using OVA absorbed to polystyrene plates. Samples are placed in wells in triplicate at a 1:25 dilution for serum. Goat anti-mouse antibody conjugated with horse radish peroxidase is used, followed by an orthophenylenediamine substrate (Sigma, St. Louis, Mo., U.S.A.). Optical density of each well is determined by placing the plate in a microtiter plate spectrophotometer and reading the plate at 490 nm. Spleen cells are tested for antibody secreting cells (ASC) specific for OVA, using techniques described previously.

The OVA specific IgG and IgA antibodies are quantified by determining the increase in optical density over time. OVA specific serum and IgA IgG and ASC secreting cells for each mouse inoculated with OVA are expected to be equally increased in those mice injected with OVA and orally fed the composition of the present invention. No OVA specific IgG or IgA antibodies are expected to be detected in mice fed antigen free composition. Thus, the composition is expected to be effective in inducing an immune response upon oral administration.

Example 11

Oral Administration of a Composition Containing Antigens to Chickens

*Salmonella enteritidis* is a major cause of disease in laying hens. Infection decreases production and increases mortality in flocks. Moreover, *S. enteritidis* can be passed through the egg to baby chicks, infecting subsequent generations or humans who consume infected eggs. Since infection begins by this bacteria attaching and invading the intestinal mucosa, and long term infection involves infection of intestinal lymphoid tissues, stimulation of mucosal immunity is imperative to control this disease.

To assess the efficacy of vaccinating chickens with the vaccine compositions of the present invention, the flagellin of *Salmonella entertidis*, a key immunogen, is incorporated within the composition according to Example 2, except that the vaccine emulsion is mixed in the alkaline sodium alginate phase at a ratio of 1:2 w/w and the slurry is spray-dried. The dry composition is top-coated on feed and administered orally to chicks. Ten-week old chickens receive 3 oral doses at 2 week intervals of the composition loaded with either 300 µg of flagellin antigen of *S. enteritidis* or Bovine serum albumin. One week after the last oral dose of antigen, serum and intestinal fluid are collected and assayed for flagellin specific antibodies by ELISA. Results are expected to show that orally vaccinated birds have significantly increased flagellin specific antibodies in the serum.

Example 12

Oral Administration of a Composition Containing Antigens to Calves

The efficacy of orally administered ovalbumin containing composition prepared in accordance with the present invention to stimulate an immune response in the lungs of calves is demonstrated.

Ovalbumin is incorporated in the composition as described in Example 1a. For oral administration to calves, a composition containing a dose of 40 µg of ovalbumin per mg is administrated in the feed. Four calves are used per experimental group and each calf receives 5 mg of ovalbumln per dose for 5 consecutive days.

Two groups of calves are used to assess the efficacy of orally administered ovalbumin to induce a specific immune response. Group 1 is given 2 doses of ovalbumin in an incomplete Freund's adjuvant by subcutaneous (SC) injection 3 weeks apart. This group serves as the parenteral control, the method of vaccination routinely used for any vaccine. Group 2 receives 2 oral regimens of a composition containing ovalbumln 3 weeks apart. Serums are evaluated for isotypic antibody response to ovalbumin. Results are expected to show that a significant amount of OVA specific IgG and IgA is produced in the orally fed calves with OVA-containing composition. The expected very high level of serum IgA predicts high effectiveness in stimulating a systemic immune response in cattle.

Example 13

Oral Administration of a Composition Containing *Vibrio* Antigens to Fish

*Vibrio alginolyticus* is a serious bacterial infection in aquaculture, particularly severe in rainbow trout. It is now endemic in all trout-producing countries where it can cause severe economic losses. It is also becoming a more significant pathogen of farmed salmon, primarily in the freshwater growing phase, but it has been reported to cause losses in the sea as well. Vaccination can prevent *V. alginolyticus* from having a significant impact at any stage of the farming cycle of salmonids. A typical vaccination program involves a primary vaccination of fry of 2-5 grams and an oral booster vaccination 4-6 months after the primary vaccination. However, an ideal vaccination program would involve only one type of vaccination provided periodically to the fish in order to maintain an effective antibody titer in the fish serum throughout the entire culture period.

Experimental design: The efficacy of orally administered ERM vaccine containing composition prepared in accordance with the present invention to stimulate an immune response in trout serum is demonstrated.

Attenuated *V. alginolyticus* is incorporated within a composition as described in Example 1b. For oral administration to fish, a composition containing a dose of 2 µg of *V. alginolyticus* vaccine per mg is administrated in the feed. Twenty fish at an average size of 5 g are used per experimental group and each fish receives 1 dose of *V. alginolyticus* vaccine in feed ration for 5 consecutive days.

Three groups of fish are used to assess the efficacy of orally administered *V. alginolyticus* vaccine to induce an immune response relative to a standard vaccination by injection. Group 1 is vaccinated using a vaccination by injection protocol. This group serves as the parenteral control, the method of vaccination routinely used for any vaccine. Group 2 receives one oral regimen of a composition containing *V. alginolyticus* vaccine. Group 3 receives one oral regimen of vaccine free composition. Sera are evaluated for isotypic antibody response to *V. alginolyticus* 6 weeks post vaccination. Results are expected to show that a significant amount of *V. alginolyticus* specific IgA is produced in the orally fed fish with *V. alginolyticus*-containing composition. The immune response in serum of both orally and injected vaccinated fish is expected to be comparable. The expected very high level of serum IgA predicts high effectiveness in stimulating a systemic immune response in fish.

Example 14

Composition Containing a Rodenticide

Warfarin is the most common rodenticide used to control rat and mouse infestations. Rodents ingesting baits containing Warfarin exhibit obvious symptoms of poisoning in 15-30 minutes and become unconscious in 1-2 hours. However, because of its fast acting effect the rodent typically ingest a sublethal amount of Warfarin and recovery occurs within 8 hours. Encapsulating the Warfarin may delay onset of the symptoms, allowing for the consumption of a full lethal dose.

Experimental Methods: Ten-twelve week old female BALB/C mice are used. Mice are fed ad libitum. Each experimental group is housed in a separate cage.

Inventive Warfarin composition: Warfarin (400 mg/g of composition, Sigma, St. Louis, Mo.) is incorporated into a composition as described generally in Example 3. Three groups of 4 mice are each fed ad libitum as follows: 1) Inventive Warfarin composition, mixed in baits at 4% Warfarin activity, 2) Unencapsulated Warfarin, mixed in baits feed at 4% activity, 3) Bait containing a composition as in Example 3, containing no Warfarin or other bioactive. The feed intake and kill effect on the mice are monitored.

Results show that feed intake of groups 1 and 3 are similar while the feed intake in group 2 (unencapsulated Warfarin) is over 25% less. It is expected that all mice in group 1 are dead after 8 h from feeding while all group 2 mice remain alive after 8 h from feeding.

What is claimed is:

1. A composition for oral administration of a bioactive agent to aquatic or terrestrial species, comprising particles each of which comprises a bioactive agent in an aqueous mixture of a mucoadhesive polymer;
    wherein said aqueous mixture of the mucoadhesive polymer and the bioactive agent is dispersed in an oil, thereby forming a water-in-oil emulsion; and
    wherein said water-in-oil emulsion is dispersed in a matrix comprising an enteric coating polymer.

2. The composition of claim 1, wherein the enteric coating polymer is crosslinked.

3. The composition of claim 2, wherein the crosslinking agent for the enteric coating polymer comprises divalent metal cations.

4. The composition of claim 1, wherein the mucoadhesive polymer is crosslinked.

5. The composition of claim 4, wherein the crosslinks in the mucoadhesive polymer are formed by association with tripolyphosphate.

6. The composition of claim 1, wherein the particles are larger than 50 μm in diameter.

7. The composition of claim 1, wherein the bioactive agent is an immunogen.

8. The composition of claim 1, wherein the mucoadhesive polymer is one or more polymers selected from the group consisting of carrageenan, chitosan, hyaluronic acid, alginate, derivatives or modifications or any of these, carboxylic-functionalized polymers, sulfate-functionalized polymers and amine-functionalized polymers.

9. The composition of claim 1, wherein the enteric coating polymer is one or more polymers selected from the group consisting of poly(meth)acrylates, alginate, pectins, carboxymethyl cellulose, methyl cellulose and cellulose acetate phthalate.

10. The composition of claim 1, wherein the enteric coating polymer matrix comprises a low viscosity grade alginate, low methoxy pectin or a combination thereof.

11. The composition of claim 1, wherein the oil is one or more oils selected from the group consisting of fats, oils and waxes.

12. The composition of claim 11, wherein the oil is a vegetable or animal oil.

13. The composition of claim 2, wherein the mucoadhesive polymer is crosslinked.

14. A method of preparing the composition of claim 2, comprising in sequence:
    (a) forming an aqueous mixture comprising a dispersed or dissolved bioactive agent;
    (b) homogenizing the aqueous mixture of step (a) in oil to produce an emulsion of the aqueous mixture in the oil at a ratio of one part aqueous mixture of step (a) to 1.1-5 parts oil by weight until a uniform emulsion is produced;
    (c) forming a slurry of the product of step (b) in an aqueous solution comprising an enteric coating polymer; and
    (d) spraying, dropping or injecting the slurry of step (c) into an aqueous solution containing a crosslinker for the enteric coating polymer to form the particles, wherein the aqueous mixture of step (a) further comprises a mucoadhesive polymer.

15. A method of preparing the composition of claim 4, comprising in sequence:
    (a) forming an aqueous mixture comprising a dispersed or dissolved bioactive agent;
    (b) homogenizing the aqueous mixture of step (a) in oil to produce an emulsion of the aqueous mixture in the oil at a ratio of one part aqueous mixture of step (a) to 1.1-5 parts oil by weight until a uniform emulsion is produced;
    (c) forming a slurry of the product of step (b) in an aqueous solution comprising an enteric coating polymer; and
    (d) forming the particles from the slurry of step (c), wherein step (b) further includes forming droplets of the emulsion in aqueous mucoadhesive polymer and crosslinking the mucoadhesive polymer to form intermediate particles.

16. The method of claim 15, wherein the step of forming the particles comprises freeze drying and milling the product of step (c).

17. The method of claim 15, wherein the step of forming the particles comprises spray drying the product of step (c).

18. A method of vaccinating aquatic or terrestrial species, comprising a step of orally administering to said species the composition of claim 1, wherein the composition is a delivery vehicle for a vaccine.

19. A method of preparing the composition of claim 13, comprising in sequence:
(a) forming an aqueous mixture comprising a dispersed or dissolved bioactive agent and forming separately an aqueous mixture of a mucoadhesive polymer;
b) mixing the aqueous mixture aqueous mixture comprising the dispersed or dissolved bioactive agent with the aqueous mixture of the mucoadhesive polymer
(c) homogenizing the aqueous mixture of step (b) in oil to produce an emulsion of the aqueous mixture in the oil at a ratio of one part aqueous mixture of step (b) to 1.1-5 parts oil by weight until a uniform emulsion is produced;
(d) cross-linking the mucoadhesive polymer in the emulsion of step c) by adding a crosslinker for the mucoadhesive polymer to the emulsion of step c);
(e) forming a slurry of the product of step (d) in an aqueous solution comprising an enteric coating polymer; and
(f) spraying, dropping or injecting the slurry of step (e) into an aqueous solution containing a crosslinker for the enteric coating polymer to form the particles.

20. A method of preparing the composition of claim 13, comprising in sequence:
(a) forming an aqueous mixture comprising a dispersed or dissolved bioactive agent
(b) homogenizing the aqueous mixture of step (a) in oil to produce an emulsion of the aqueous mixture in the oil at a ratio of one part aqueous mixture of step (a) to 1.1-5 parts oil by weight until a uniform emulsion is produced;
(c) forming droplets of the emulsion of step (a) in an aqueous mucoadhesive polymer solution;
d) cross-linking the mucoadhesive polymer in the emulsion of step (c) by adding a crosslinker for the mucoadhesive polymer to the emulsion of step (c);
(e) forming a slurry of the product of step (d) in an aqueous solution comprising an enteric coating polymer; and
(f) forming the particles from the slurry of step (e).

* * * * *